(12) United States Patent
Tretjak et al.

(10) Patent No.: US 9,908,838 B2
(45) Date of Patent: Mar. 6, 2018

(54) PROCESS FOR PRODUCING LIGHT (METH)ACRYLIC ESTERS

(71) Applicant: Arkema France, Colombes (FR)

(72) Inventors: Serge Tretjak, Roulhing (FR); Stephane Denis, Leyviller (FR); Lionel Delais, Senlis (FR); Anne Moreliere, Longeville-les-St-Avold (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 15/032,864

(22) PCT Filed: Oct. 21, 2014

(86) PCT No.: PCT/FR2014/052667
§ 371 (c)(1),
(2) Date: Apr. 28, 2016

(87) PCT Pub. No.: WO2015/063388
PCT Pub. Date: May 7, 2015

(65) Prior Publication Data
US 2016/0272570 A1    Sep. 22, 2016

(30) Foreign Application Priority Data

Oct. 29, 2013  (FR) .................................. 13 60541
Feb. 10, 2014  (FR) .................................. 14 50994

(51) Int. Cl.
| C07C 67/48 | (2006.01) |
| C07C 67/08 | (2006.01) |
| C07C 45/52 | (2006.01) |
| C07C 51/44 | (2006.01) |
| C07C 51/487 | (2006.01) |
| C07C 67/54 | (2006.01) |
| C07C 67/58 | (2006.01) |

(52) U.S. Cl.
CPC .............. *C07C 67/08* (2013.01); *C07C 45/52* (2013.01); *C07C 51/44* (2013.01); *C07C 51/487* (2013.01); *C07C 67/54* (2013.01); *C07C 67/58* (2013.01); *Y02P 20/582* (2015.11)

(58) Field of Classification Search
None
See application file for complete search history.

(56) References Cited

U.S. PATENT DOCUMENTS

| 3,776,947 A | 12/1973 | Shimizu |
| 3,868,410 A | 2/1975 | Horlenko |
| 3,914,290 A | 10/1975 | Otsuki |
| 4,435,594 A | 3/1984 | Matasmura |
| 4,464,229 A | 8/1984 | Sato |
| 6,025,520 A | 2/2000 | Suzuki |
| 2005/0107629 A1 | 5/2005 | Hershberger |
| 2008/0161596 A1* | 7/2008 | Riondel ............... C07C 213/06 560/155 |

FOREIGN PATENT DOCUMENTS

GB    2016461    9/1979

OTHER PUBLICATIONS

International Search Report and Written Opinion for International Application No. PCT/FR2014/052667, dated Feb. 2, 2015, 10 pages.

* cited by examiner

*Primary Examiner* — Sudhakar Katakam
*Assistant Examiner* — Ana Z Muresan
(74) *Attorney, Agent, or Firm* — RatnerPrestia

(57) ABSTRACT

The subject matter of the present invention is an improvement in the continuous production of methyl (meth)acrylate or of ethyl (meth)acrylate by direct esterification of (meth) acrylic acid with methanol or ethanol, under reaction conditions for which the acid is in excess relative to the alcohol, in particular with an acid/alcohol molar ratio of between 1.0 and 4, and under a pressure ranging from atmospheric pressure to 5 bar. The process of the invention makes it possible to minimize the formation of ethyl ethoxypropionate during the esterification reaction, and results in an improvement in the material balance, simplification of the purification train for the desired ester, and optimization of the energy balance.

14 Claims, 2 Drawing Sheets

PROCESS FOR PRODUCING LIGHT (METH)ACRYLIC ESTERS

CROSS-REFERENCE TO RELATED APPLICATIONS

This is the national phase of International Application No. PCT/FR2014/052667, filed 21 Oct. 2014, which claims priority from French Application Nos. 1360541 and 1450994, filed 29 Oct. 2013 and 10 Feb. 2014, respectively. The disclosure of each of these applications is incorporated herein by reference in its entirety for all purposes.

TECHNICAL FIELD

The present invention relates to the production of light (meth)acrylic esters, and the subject of the invention is more particularly an improvement in the continuous production of methyl (meth)acrylate or ethyl (meth)acrylate by direct esterification of (meth)acrylic acid by methanol or ethanol, under reaction conditions in which the acid is in excess relative to the alcohol.

PRIOR ART AND TECHNICAL PROBLEM

It is known practice to produce (meth)acrylic esters, especially methyl acrylate or methacrylate and ethyl acrylate or methacrylate, by direct esterification of (meth)acrylic acid by the corresponding alcohol, catalyzed for example by sulfuric acid or an ion exchange resin. Mention may be made for example of the processes described in documents U.S. Pat. No. 3,776,947; U.S. Pat. No. 3,914,290; U.S. Pat. No. 4,464,229 or U.S. Pat. No. 4,435,594, in which the alcohol is used in excess relative to the (meth)acrylic acid.

The esterification reaction generates water, and is generally accompanied by side reactions which produce impurities, in particular heavy compounds, that is to say compounds having a high boiling point, greater than that of the ester which is sought.

In such processes, for environmental and economic reasons, it is vital to recycle unreacted reagents—predominantly alcohol and also acid—to the reaction, but also to recover value from the heavy products generated during the process, while seeking a final product of high purity.

To these ends, a set of treatments are generally carried out on the reaction mixture by means of distillations and/or extractions or settling out operations, which set of treatments is relatively complex to carry out, costly in terms of energy, and has the drawback of generating a final residue without recoverable value, which may represent a loss in raw materials.

The problems which arise during the manufacture of light (meth)acrylic esters, especially the formation of heavy by-products, will now be detailed, for convenience's sake, on the basis of the example of ethyl acrylate obtained by esterification of acrylic acid by ethanol. However, the problems and the solution proposed by the invention are the same in the case of the use in the esterification reaction, on the one hand, of methacrylic acid or, on the other hand, of methanol.

In terms of side reactions leading to the formation of heavy by-products during the manufacture of ethyl acrylate, these are essentially the formation of oligomers of unreacted acrylic acid—acrylic acid dimer (3-acryloxypropionic acid, n=1) and to a lesser extent acrylic acid trimer (3-(3-acryloxypropyloxy)propionic acid, n=2)—but are also Michael addition reactions (Michael adducts), in particular between already formed ethyl acrylate and unreacted ethanol, leading to ethyl ethoxypropionate.

Ethyl ethoxypropionate (EEP) is a "heavy" by-product since its boiling point (168° C., atmospheric pressure) is considerably higher than that of ethyl acrylate (100° C., atmospheric pressure), and it becomes concentrated in the process as the reaction proceeds, at the same time as the acrylic acid oligomers. Since its boiling point is close to that of acrylic acid (144° C., atmospheric pressure), EEP will moreover become concentrated in the recycling loop for the unreacted acrylic acid, and necessitate a purge of this recycling loop; a significant portion of acrylic acid is then lost during the purge unless thermal cracking of the purged stream is carried out to regenerate the acrylic acid present in the form of oligomers, this thermal cracking not having any effect on the EEP, however. Moreover, since EEP is the lightest of the heavy by-products, its presence in the reaction medium will interfere in the final purification of the ethyl acrylate.

It was proposed, in the process for synthesizing ethyl acrylate described in document US 2005/0107629, to carry out a purge of the reactor, the purged stream being sent to a distillation unit for separating a distillate containing acrylic acid, ethyl acrylate and ethanol, which is recycled to the reaction, and a residue which is subjected to a unit for recovering the esterification catalyst. This process makes it possible to avoid an accumulation of heavy by-products in the reactor and to recycle the compounds with directly recoverable value and which are present in the purged stream, but it represents a significant loss of acrylic acid present in the form of oligomers and/or ethyl ethoxypropionate in the purged stream.

In document U.S. Pat. No. 6,025,520, it is proposed to carry out the esterification reaction between (meth)acrylic acid and an alcohol comprising from 1 to 3 carbon atoms, catalyzed by a highly acidic ion exchange resin, under reduced pressure and with an alcohol/acid mole ratio of less than 1, preferably ranging from 0.3 to less than 1. These conditions make it possible to improve the yield and the selectivity of the esterification reaction and to significantly reduce the formation of heavy by-products such as methyl methoxypropionate (in the case in which the alcohol is methanol), the presence of which is moreover problematic for the purification line for the ester which is sought.

However, despite the advances brought by this process, implementing the reaction conditions still has numerous drawbacks: on the one hand, this process requires working under reduced pressure in the reaction assembly, and consequently requires specific reactor technology since the reaction medium becomes two-phase (gas/liquid) or even three-phase under conditions of heterogeneous catalysis; on the other hand, the hourly space velocity (HSV) of the stream undergoing the reaction, defined as the ratio between the flow rate of the reaction stream and the volume of the catalyst, ranges from 0.1 h$^{-1}$ to less than 1 h$^{-1}$, which means that for equal ester production, the amount of catalyst employed may vary by a factor of 10, or which corresponds to a residence time in the reactor of more than one hour, possibly rising as far as ten hours. The examples illustrating this process, and also the comparative example carried out under atmospheric pressure, were carried out with an HSV of 0.33 h$^{-1}$ corresponding to a residence time of 3 hours in the reactor.

Document GB 2 016 461 described a method for producing an ester by esterification reaction of an alcohol with an excess of acid. The method is illustrated with isobutyric and methacrylic acids. The methyl methacrylate is synthesized in particular with a stream containing 11 wt % of methanol and 88.8 wt % of methacrylic acid, corresponding to a stoichiometric excess of acid of approximately 3, and with a residence time of 20 minutes in the reactor. The purified methyl methacrylate is separated after a two-step purification process employing two distillation columns.

There therefore remains a real need to overcome the drawbacks of the processes for synthesizing light (meth) acrylates of the prior art, especially to minimize the formation of ethyl ethoxypropionate in the case of ethyl acrylate synthesis, which is detrimental to the material balance of the process (loss of raw materials) and to the purity of the product which is sought (complexity of the purification line), in a simplified process configuration.

Surprisingly, the inventors discovered that it was possible to significantly reduce the formation of ethyl ethoxypropionate in conventional fixed bed reactor technology by carrying out the esterification reaction under conditions in which the acid is in excess relative to the alcohol, and under atmospheric pressure. With these conditions, it is possible to use the fixed bed reactors already used for the reactions carried out with an excess of alcohol, since the nature of the reaction stream kept in liquid phase and the necessary residence time are not modified.

In addition, the inventors found that the formation of adducts could furthermore be significantly reduced by minimizing the amount of water introduced into the reactor, the water possibly coming from the alcohol feed or from the recycling of the stream comprising unreacted acid and/or unreacted alcohol with a fraction of the water generated by the esterification reaction.

One of the aims of the present invention is therefore to provide a process for synthesizing ethyl acrylate, and more generally methyl (meth)acrylate or ethyl (meth)acrylate, which minimizes the formation of ethyl ethoxypropionate during the esterification reaction, this process leading to the improvement of the material balance, simplification of the purification line for the ester which is sought, and optimization of the energy balance.

The process of the invention is particularly advantageous in relation to the process described in U.S. Pat. No. 6,025,520 since the esterification reaction is carried out at atmospheric pressures with higher hourly space velocities leading to higher productivity.

SUMMARY OF THE INVENTION

A subject of the present invention is a process for synthesizing methyl (meth)acrylate or ethyl (meth)acrylate by esterification of (meth)acrylic acid with the corresponding alcohol in the presence of an acidic catalyst, characterized in that the esterification reaction is carried out in a reactor at an acid/alcohol mole ratio of between 1.05 and 4 and at a pressure ranging from atmospheric pressure to 5 bar, and with a residence time of the stream undergoing the reaction of between 30 minutes and 1 hour.

The term "between" is intended to include the limit values within the meaning of the invention.

"(Meth)acrylic acid" is intended to mean acrylic acid or methacrylic acid. Preferably, the reaction acid is acrylic acid.

Preferably, the alcohol is ethanol.

The reaction temperature is generally between 60° C. and 90° C.

The process according to the invention is advantageously implemented in fixed bed reactor technology, preferably with a solid catalyst of ion exchange resin type, or a stirred reactor, preferably with a liquid catalyst of sulfuric acid type or organic sulfonic acid type.

The hourly space velocity for the reaction stream is between $1\ h^{-1}$ and $2\ h^{-1}$.

According to one embodiment, the process according to the invention may comprise steps of dehydrating the stream, by any known technique, making it possible to reduce the water content at the inlet to the reactor, which consequently reduces adduct formation.

According to this embodiment, the process comprises at least one step of dehydrating a stream feeding the reactor.

Said dehydration step may be applied to at least one of the following streams: the fresh alcohol feed stream, a recycling stream for the unreacted alcohol, or a recycling stream for the unreacted acid.

According to one embodiment, the process according to the invention comprises the following steps:
  a) feeding a reactor with (meth)acrylic acid, acidic catalyst and alcohol, and the esterification reaction in the reactor as defined above;
  b) drawing off a stream of methyl (meth)acrylate or ethyl (meth)acrylate at the reactor outlet;
  c) distilling the stream of methyl (meth)acrylate or ethyl (meth)acrylate, making it possible to separate, at the top, a stream of (meth)acrylate depleted of heavy by-products and of unreacted (meth)acrylic acid, and at the bottom, a stream comprising the heavy by-products, unreacted (meth)acrylic acid and traces of alcohol and of light products;
  d) separating the bottom stream obtained in step c) into a stream comprising unreacted (meth)acrylic acid and traces of alcohol and of light products, this stream being recycled into the reactor, and a stream of heavy by-products which is subjected to a thermal cracking which releases a stream of products with recoverable value which returns to step d);
  e) liquid-liquid extraction of the top stream obtained in step c) by an aqueous stream making it possible to separate a purified organic phase of methyl (meth)acrylate or ethyl (meth)acrylate and an aqueous phase, the aqueous phase being distilled to recover, on the one hand, an alcohol-rich fraction which is recycled to the reactor, and on the other hand, a water-rich fraction which is used as aqueous stream in the liquid-liquid extraction step.

The process according to the invention may also comprise one or more steps for distilling the purified organic phase of methyl (meth)acrylate or ethyl (meth)acrylate in order to eliminate additional organic compounds.

The process according to the invention may also comprise a step f) comprising dehydrating at least one of the following streams: the alcohol feed from step a), the flow comprising unreacted (meth)acrylic acid obtained in step d) or the alcohol-rich distilled fraction obtained in step e).

The present invention makes it possible to overcome the drawbacks of the prior art. It more particularly provides a means for limiting the problems associated with the presence of by-products without recoverable value in a process for synthesizing methyl (meth)acrylate or ethyl (meth)acrylate, the products with recoverable value being unreacted reagents or the ester which is sought (noble products) or the heavy by-products such as acrylic acid oligomers which are capable of releasing noble products.

This is achieved by the choice of operating conditions, in particular by carrying out the esterification reaction with an acid/alcohol mole ratio of between 1.05 and 4, preferably between 1.05 and 3, and under a pressure ranging from atmospheric pressure to 5 bar.

In addition, by minimizing the amount of water entering the esterification reactor, the reduction in the amount of heavy by-products and in particular of adducts formed during the synthesis is further enhanced.

This is because the inventors have discovered that, under these conditions, by-products without recoverable value are generated in a small amount, which brings about the following advantages for the overall process: much simpler value recovery from heavy products or products having a higher boiling point than acrylic acid (in particular acrylic acid oligomers), simplification of the final purification line for the ester formed, including a reduced number of distillation columns, and low energy consumption because the amount of alcohol to be recycled is lower.

Thus, the invention makes it possible to employ a simplified facility to produce high-purity methyl (meth)acrylates or ethyl (meth)acrylates and it optimizes the material balance of the process.

DETAILED DESCRIPTION OF THE INVENTION

Figure 1:
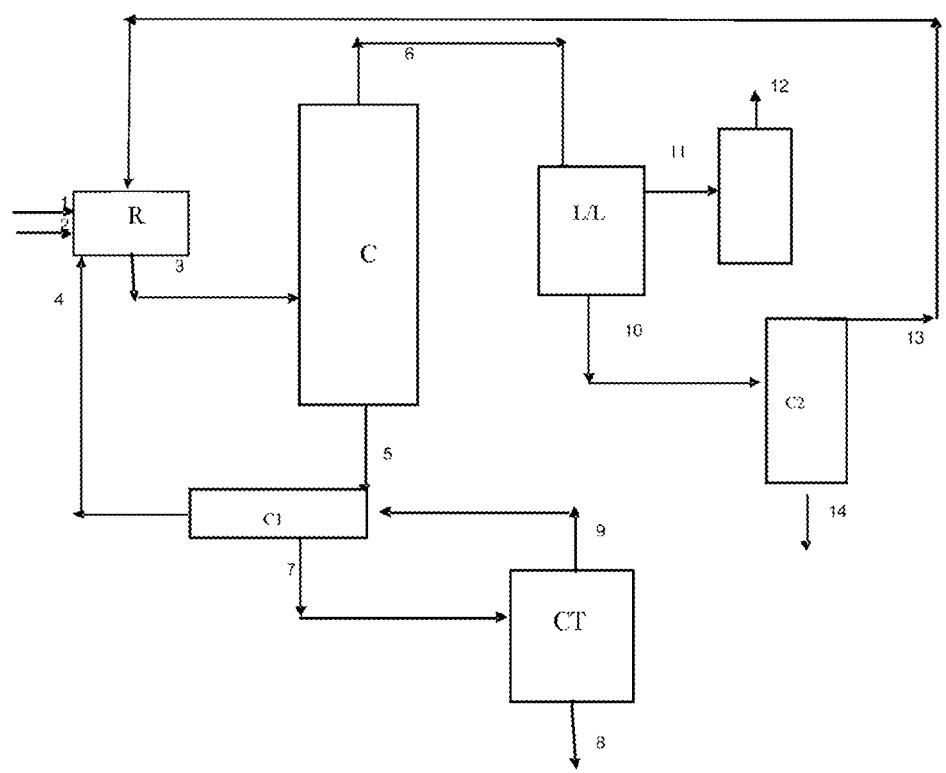
FIG. 1 schematically represents a facility for implementing the process according to the invention, applied in particular to the synthesis of ethyl acrylate.

The invention is now described in more detail and non-limitingly in the following description.

According to the invention, the acid/alcohol mole ratio refers to the contents of acid and alcohol in all of the streams feeding the esterification reactor (stream of pure products and recycled streams).

According to one preferred embodiment, the (meth) acrylic acid/alcohol mole ratio in the reactor is between 1.05 and 3, more preferably between 1.5 and 3, or even between 2 and 2.5.

According to one preferred embodiment, the pressure is chosen between atmospheric pressure and 3 bar.

The esterification reaction is carried out in the presence of an acidic catalyst, for example an acidic cation exchange resin in the case of heterogeneous catalysis; or, as catalyst in the case of homogeneous catalysis, it is possible to use for example sulfuric acid or an organic sulfonic acid such as methanesulfonic acid, para-toluenesulfonic acid, benzenesulfonic acid, dodecylsulfonic acid or mixtures thereof.

The reaction is carried out in the presence of one or more polymerization inhibitors which are introduced into the reactor in an amount of 500 to 5000 ppm relative to the crude reaction mixture. As polymerization inhibitors which may be used, mention may be made for example of phenothiazine, hydroquinone, hydroquinone monomethyl ether, di-tert-butyl-para-cresol (BHT), para-phenylenediamine, TEMPO (2,2,6,6-tetramethyl-1-piperidinyloxy), di-tert-butylcatechol, or derivatives of TEMPO, such as OH-TEMPO, alone, or mixtures thereof in any proportions. A supplementary addition of polymerization inhibitor is generally carried out at the subsequent purification treatment.

In general, water is introduced into the reactor in a not insignificant amount in various forms:

On the one hand, the quality of industrial alcohol used as reagent generally comprises water at a content of the order of 5 to 10 weight %.

On the other hand, the streams containing unreacted alcohol and/or acid coming from the purification line for the reaction medium comprising the product which is sought and water are generally recycled to the reaction. The alcohol recycling stream may then comprise from 10 to 60 weight % of water and the acid recycling stream may comprises from 2 to 20% of water.

According to one preferred embodiment of the invention, the amount of water at the inlet of the reactor may be limited by installing a dehydration system on one or more of these streams.

The dehydration system may be any system, able to separate water from a more or less complex medium, which is known by those skilled in the art.

Mention may be made, by way of example, of a membrane separation unit, more particularly a unit for dehydration by pervaporation or vapor permeation. According to this embodiment, the unit for dehydration by membrane separation may comprise an inorganic membrane, preferably a zeolite membrane, and more particularly preferably a zeolite T membrane, or a polymeric membrane, preferably a hydrophilic membrane based on polyvinyl alcohol.

Alternatively, it is possible to use a pressure swing adsorption (PSA) system such as that known for the dehydration of alcohols.

Otherwise, it is possible to eliminate most of the water by simple distillation.

It is understood that it is possible to use different dehydration systems within the same process.

According to this embodiment, it is possible to reduce the water introduced into the reactor by about 85%, which lowers the water content at the inlet of the reactor to approximately 0.8-1.5 weight % instead of 5-10 weight % in the absence of a dehydration unit. This reduction is significant for having a beneficial effect on adduct formation during synthesis.

With reference to FIG. 1, a facility for producing ethyl acrylate according to the invention comprises a reactor R. The reactor R is fed by a pipe for feeding acrylic acid 1 and a pipe for feeding ethanol 2. The reactor preferably contains an acidic cation exchange resin type catalyst. In the case of homogeneous catalysis, the reactor is also feed by a pipe for feeding catalyst (not depicted).

At the outlet of the reactor, the reaction mixture 3 is sent to a distillation column C which separates, at the bottom, a stream 5 essentially comprising the unreacted acrylic acid, traces of light products (boiling point lower than that of acrylic acid) and the products having a higher boiling point than acrylic acid (oligomers of acrylic acid and Michael adducts), referred to below as adducts, and, at the top, a stream 6 comprising the ethyl acrylate formed and lighter products than acrylic acid (unreacted ethanol, by-products such as ethyl acetate and acetic acid).

The bottom stream 5 from column C is sent to a distillation column C1 which separates a stream 4 comprising the residual acrylic acid and the lighter products, this stream 4 being recycled into the reactor R. A stream 7 essentially consisting of heavy products (adducts) is separated from the column C1 and subjected to a thermal cracking in the thermal cracker CT.

As distillation column C or C1, use may be made of a column comprising internals of the random or ordered packing type, of the dual flow tray type, perforated tray with downcomer type, or valve tray type. It is also possible to install a film evaporator instead of the column C1.

Thermal cracking makes it possible to recycle the noble products (starting compounds or final product) which may potentially be recovered from the heavy product fraction. The thermal cracking is carried out at a temperature which may range for example from 120° C. to 220° C., optionally in the presence of an acidic catalyst such as sulfuric acid or a sulfonic acid. The effect of thermal cracking is to release the starting compounds, essentially acrylic acid, which are present in the adducts, but it has little effect on the ethyl ethoxypropionate which, because of this, remains partly present at the outlet of the thermal cracker in stream 9 of acrylic acid which is recycled to the column C1, the rest of the ethyl ethoxypropionate being in the stream 8 with the other heavy products without recoverable value, stream 8 being incinerated.

Stream 6 from the top of the distillation column C is sent to a liquid-liquid extraction section (decanter or contactor) to generate, on the one hand, an aqueous phase 10 containing ethanol which is recycled to the reaction (stream 13) following distillation in a column C2 (the ethanol-depleted aqueous stream 14 possibly being recycled for the liquid-liquid extraction phase), and on the other hand, an organic phase 11.

The liquid-liquid extraction section may consist of a liquid-liquid extraction column of stirred or packed column type, a mixer-decanter battery, or one or more decanters in series.

The organic phase 11 may be subjected to one or more supplemental distillation steps to give the purified ethyl acrylate 12. However, the process according to the invention makes it possible to simplify this final scheme for rectifying the ester which is sought and thus it is possible to more easily achieve the desired specifications, especially in terms of residual content of ethyl ethoxypropionate.

The dehydration units (not represented on the figure) aiming to reduce the amount of water introduced into the reactor, as described above, may be installed on line 2 for feeding fresh alcohol, on line 13 for recycling alcohol or on line 4 for recycling acid.

The following examples illustrate the present invention and do not aim to limit the scope of the invention as defined by the appended claims.

EXPERIMENTAL SECTION

Example 1

Tests for synthesizing ethyl acrylate were carried out using a reactor 2.5 cm in diameter, 55 cm high and with a volume of 270 ml. The reactor is filled with 330 ml of K1431 resin (LANXESS). Before being placed in the reactor, the resin (330 ml) was conditioned in the reaction mixture, leading to a reduction in volume by replacing the water in its structure with the reagents present in the reaction mixture.

The reagents are introduced at the top of the reactor via a pump. They may be preheated to the reaction temperature. At the bottom of the reactor there is a condenser which cools the reaction mixture by virtue of a calender fed with water. The pressure is regulated by acting on a regulating valve placed at the outlet of the condenser.

The reaction mixture is stabilized with 1000 ppm of hydroquinone and placed under stirring. To take account of the streams derived from recycling operations, the reactor was fed with a synthetic mixture comprising, in weight %: 1.5% of water, 65%-75% of acrylic acid (AA), 20%-28% of ethanol (EtOH), 2.5% to 4% of ethyl acrylate (EA) and impurities such as ethyl acetate (45 ppm), acetic acid and hydroquinone in an amount of 1000 ppm.

The composition of the synthetic mixture is readjusted so as to vary the AA/EtOH mole ratio from 1.5 to 2.5.

The feed flow rate varies such that the residence time (feed flow rate/volume of resin before conditioning) varies between 45 mins and 60 mins. The reactor is heated and the feed mixture is preheated such that the reaction is carried out at 75° C. or at 85° C., and the pressure is fixed at 2 bar.

Analyses are carried out by GC and HPLC from samples taken from the reaction medium. The water content is determined by Karl Fischer titration and the acrylic acid content may optionally be determined by potentiometry.

The results are expressed in the following way:

Conversion of the reagent (AA or EtOH), %=100−(number of moles of reagent remaining/number of moles of reagent introduced).

EA selectivity, %=100×number of moles of EA produced/number of moles of reagent having reacted.

Amount in kg of heavy by-products formed (adducts) per ton of EA produced.

Amount in kg of adducts with recoverable value per ton of EA produced.

Amount in kg of adducts without recoverable value per ton of EA produced

Amount in kg of ethyl ethoxypropionate (EEP) formed per ton of EA produced.

The results of the various tests are collated in tables 1 to 3 below.

TABLE 1

| AA/EtOH mole ratio | Temperature (° C.) | Residence time (min) | EtOH conversion (%) | Selectivity for EA relative to EtOH (%) |
|---|---|---|---|---|
| 1.5 | 85 | 60 | 72.8 | 97.1 |
|  |  | 45 | 69.6 | 97.3 |
|  | 75 | 60 | 63.8 | 97.6 |
|  |  | 45 | 58.5 | 97.8 |
| 2 | 85 | 60 | 81.9 | 97.1 |
|  |  | 45 | 79.6 | 97.3 |
|  | 75 | 60 | 73.8 | 97.8 |
|  |  | 45 | 68.7 | 97.9 |
| 2.5 | 85 | 60 | 86.6 | 97.3 |
|  |  | 45 | 84.5 | 97.5 |
|  | 75 | 60 | 81 | 97.8 |
|  |  | 45 | 76.4 | 97.9 |

Ethanol conversion varies from 58.5% to 86.6% and selectivity for ethyl acrylate relative to ethanol is always greater than 97%.

TABLE 2

| AA/EtOH mole ratio | Temperature (° C.) | Residence time (min) | AA conversion (%) | Selectivity for EA relative to AA (%) |
|---|---|---|---|---|
| 1.5 | 85 | 60 | 47.2 | 97.7 |
|  |  | 45 | 45.5 | 98.1 |
|  | 75 | 60 | 41.8 | 98.3 |
|  |  | 45 | 38.4 | 98.5 |
| 2 | 85 | 60 | 40.4 | 97 |
|  |  | 45 | 39.4 | 97.6 |
|  | 75 | 60 | 37.1 | 98.1 |
|  |  | 45 | 34.2 | 98.3 |

TABLE 2-continued

| AA/EtOH mole ratio | Temperature (° C.) | Residence time (min) | AA conversion (%) | Selectivity for EA relative to AA (%) |
|---|---|---|---|---|
| 2.5 | 85 | 60 | 36.6 | 96.5 |
|  |  | 45 | 34.9 | 97.3 |
|  | 75 | 60 | 32.5 | 97.8 |
|  |  | 45 | 30.7 | 98.1 |

Acrylic acid conversion varies from 30.7% to 47.2% and it is linked to the presence of the stoichiometric excess of the acidic reagent. Selectivity for ethyl acrylate relative to acrylic acid ranges from 96.5% to 98.5%.

TABLE 3

| AA/EtOH mole ratio | Temperature (° C.) | Residence time (min) | Total adducts (kg/t) | Adducts with recoverable value (kg/t) | Adducts without recoverable value (kg/t) | EEP (kg/t) |
|---|---|---|---|---|---|---|
| 1.5 | 85 | 60 | 28.9 | 3.9 | 25 | 12 |
|  |  | 45 | 25.9 | 2.5 | 23.4 | 12 |
|  | 75 | 60 | 22.3 | 2.6 | 19.7 | 10.5 |
|  |  | 45 | 20.2 | 2 | 18.2 | 10.1 |
| 2 | 85 | 60 | 33.8 | 9.6 | 24.2 | 10.1 |
|  |  | 45 | 29.4 | 6.8 | 22.5 | 10.1 |
|  | 75 | 60 | 23.4 | 4.5 | 18.9 | 9.1 |
|  |  | 45 | 21.3 | 3.8 | 17.5 | 8.8 |
| 2.5 | 85 | 60 | 38.7 | 15.3 | 23.3 | 8.6 |
|  |  | 45 | 31.7 | 10.2 | 21.5 | 8.7 |
|  | 75 | 60 | 25.4 | 7.3 | 18.1 | 7.9 |
|  |  | 45 | 22.9 | 5.9 | 17 | 7.9 |

The AA/EtOH influences the total amount of adducts formed during the esterification reaction. When the acrylic acid is in excess in the reaction stream, the total content of adducts formed increases. However, it was observed that at the same time the amount of adducts without recoverable value, in particular ethyl ethoxypropionate, decreases when the AA/EtOH mole ratio increases. The loss of raw materials linked to the elimination of adducts without recoverable value is therefore reduced when esterification is carried out with a large stoichiometric excess of acrylic acid.

Indeed, on average, 0.5 kg to 1 kg less of adducts without recoverable value are produced per ton of ethyl acrylate produced for an increase in the AA/EtOH mole ratio of 0.5; this reduction, scaled up to an industrial level, for example a unit which may produce 100000 t/year of ethyl acrylate, leads to a gain of 50 t to 100 t in raw materials arising directly from this increase in the mole ratio.

The reduction in the formation of ethyl ethoxypropionate will also produce effects on the steps of final purification of the ethyl acrylate, by facilitating the ease with which the specification sought in terms of content of residual EEP is obtained (generally <50 ppm).

Figure 2:
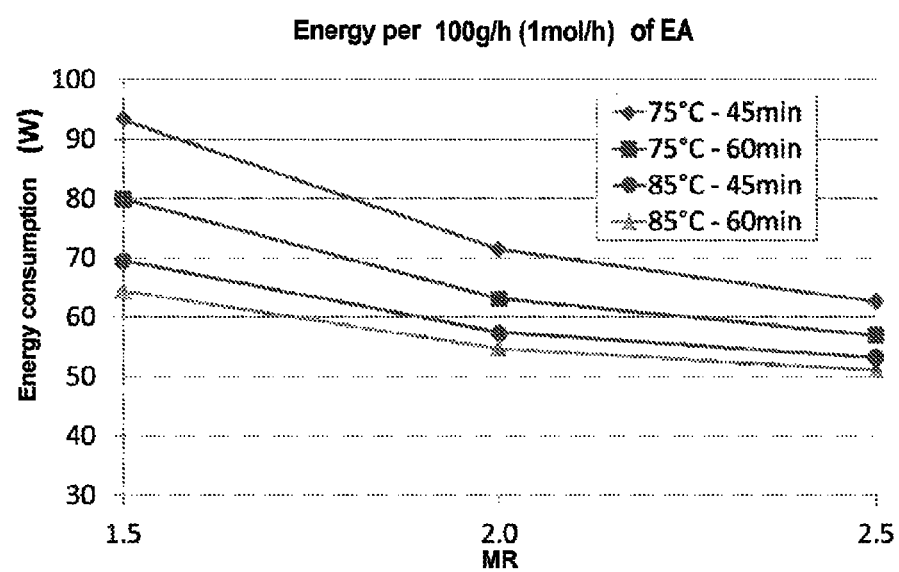
FIG. 2 illustrates the energy gain for recycling ethanol obtained with the process according to the invention.

Moreover, FIG. 2 illustrates the energy gain obtained by the process according to the invention.

Recycling unreacted ethanol necessitates withdrawing it from the reaction medium with water and distilling the aqueous solution of ethanol. In the process according to the invention, based on an excess of acidic reagent, the amount of unreacted alcohol is reduced and consequently it can be recycled with a smaller amount of energy.

FIG. 2 represents the energy consumption linked to ethanol recycling, applied to production of 100 g/h of ethyl acrylate, as a function of the AA/EtOH mole ratio (MR) under the synthesis conditions (temperature, residence time) described above. The energy gain is always greater than 20% when MR varies from 1.5 to 2.5.

Example 2: Effect of Acid/Alcohol Mole Ratio on the Formation of Ethyl Ethoxypropionate To illustrate the beneficial effect of the excess of acrylic acid on the formation of EEP, comparative tests were carried out in the same equipment as used in example 1, with a K1431 resin volume of 206 ml, a reaction temperature of 75° C. at a pressure of 1.3 bar and a residence time of 110 mins.

Table 4 below shows the beneficial effect of the AA/EtOH mole ratio on reducing the formation of EEP. The negative effect of a residence time greater than one hour for the formation of EEP is also observed (compared to the results from table 3 obtained with shorter residence times).

TABLE 4

| AA/EtOH Mole ratio | Temperature (° C.) | Residence time (min) | EEP (kg/t) |
|---|---|---|---|
| 2.3 | 75 | 110 | 19 |
| 1.4 | 75 | 110 | 20 |
| 1 (comp) | 75 | 110 | 22.6 |
| 0.8 (comp) | 75 | 110 | 24 |
| 0.5 (comp) | 75 | 110 | 28 |
| 0.19 (comp) | 75 | 110 | 35 |

Example 3: Effect of Water on Process Productivity

Tests for synthesizing ethyl acrylate were carried out under the same conditions as those from example 1, with a feed stream composed, in weight %, of 0.5 to 6% of water, 65%-75% of acrylic acid, 20-28% of ethanol, 0 to 3% of ethyl acrylate and impurities such as ethyl acetate (45 ppm), acetic acid and hydroquinone in an amount of 1000 ppm.

The water content was varied so as to simulate an at least partially dehydrated stream for feeding the reactor.

In these tests, the reaction temperature is 75° C. and the residence time in the reactor is 45 mins.

The results of the tests are collated in table 5 below.

TABLE 5

| AA/EtOH mole ratio | H$_2$O % | EA % | Total adducts (g/100 g EA) | Adducts with recoverable value (%) | ETOH conversion (%) | Selectivity for EA relative to EtOH (%) | Selectivity for EA relative to AA (%) |
|---|---|---|---|---|---|---|---|
| 2.5 | 0.6 | 0 | 2.2 | 26 | 76 |  |  |
| 2.5 | 3 | 0 | 2.5 | 26 | 69 | 97 | 97.5 |
| 2.5 | 5.7 | 0 | 2.7 | 23 | 61 |  |  |
| 2 | 1 | 3 | 2.1 | 17 | 69 | 97.9 | 98.3 |

In these conditions, when the water content in the feed stream of the esterification reactor is reduced (from 5.7% which represents a conventional content in esterification processes to 0.6% which may be obtained after membrane separation of the water present in a recycled stream), alcohol conversion increases (from 61% to 76%) and selectivity for EA relative to ethanol or acrylic acid is improved.

It was observed that the amount of adducts formed decreases (2.7 to 2.2 g/100 g of EA produced) while the proportion of adducts with recoverable value for example by heat treatment increases (23% to 26%). Consequently, the formation of ethyl ethoxypropionate with no recoverable value is reduced, which facilitates the purification line for the ethyl acrylate and improves the material balance of the process.

The invention claimed is:

1. A process for synthesizing methyl (meth)acrylate or ethyl (meth)acrylate by esterification of (meth)acrylic acid with the corresponding alcohol in the presence of an acidic catalyst, wherein the esterification reaction is carried out in a reactor at an acid/alcohol mole ratio of between 1.05 and 4 at a pressure ranging from atmospheric pressure to 5 bar, and with a residence time of the stream undergoing the reaction of between 30 minutes and 1 hour.

2. The process as claimed in claim 1, wherein the acid/alcohol mole ratio is between 1.5 and 3.

3. The process as claimed in claim 1, wherein the pressure ranges from atmospheric pressure to 3 bar.

4. The process as claimed in claim 1, wherein the (meth)acrylic acid is acrylic acid.

5. The process as claimed in claim 1, wherein the alcohol is ethanol.

6. The process as claimed in claim 1, the esterification is carried out at a reaction temperature of between 60° C. and 90° C.

7. The process as claimed in claim 1, wherein the reactor is a fixed bed reactor or a stirred reactor.

8. The process as claimed in claim 1, wherein the process comprises at least one step of dehydrating a stream feeding the reactor.

9. The process as claimed in claim 8, wherein the dehydration step is applied to at least one of the following streams: a fresh alcohol feed stream, a recycling stream for unreacted alcohol, or a recycling stream for unreacted acid.

10. The process as claimed in claim 8, wherein the dehydration step is carried out by membrane separation, by distillation or by pressure swing adsorption.

11. A process for synthesizing methyl (meth)acrylate or ethyl (meth)acrylate by esterification of (meth)acrylic acid with the corresponding alcohol in the presence of an acidic catalyst, wherein the process comprises the following steps:
    a) feeding a reactor with (meth)acrylic acid, acidic catalyst and alcohol, and the esterification reaction in the reactor is carried out in accordance with claim 1;
    b) drawing off a stream of methyl (meth)acrylate or ethyl (meth)acrylate at the reactor outlet;
    c) distilling the stream of methyl (meth)acrylate or ethyl (meth)acrylate, making it possible to separate, at the top, a stream of (meth)acrylate depleted of heavy by-products and of unreacted (meth)acrylic acid, and at the bottom, a stream comprising the heavy by-products, unreacted (meth)acrylic acid and traces of alcohol and of light products;
    d) separating the bottom stream obtained in step c) into a stream comprising unreacted (meth)acrylic acid and traces of alcohol and of light products, this stream being recycled into the reactor, and a stream of heavy by-products which is subjected to a thermal cracking which releases a stream of products with recoverable value which returns to step d);
    e) liquid-liquid extraction of the top stream obtained in step c) by an aqueous stream making it possible to separate a purified organic phase of methyl (meth)acrylate or ethyl (meth)acrylate and an aqueous phase, the aqueous phase being distilled to recover, on the one hand, an alcohol-rich fraction which is recycled to the reactor, and on the other hand, a water-rich fraction which is used as aqueous stream in the liquid-liquid extraction step;
    f) optionally dehydrating at least one of the following streams: the alcohol feed from step a), the flow comprising unreacted (meth)acrylic acid obtained in step d) or the alcohol-rich distilled fraction obtained in step e).

12. The process as claimed in claim 11, also comprising one or more steps for distilling the purified organic phase of methyl (meth)acrylate or ethyl (meth)acrylate in order to eliminate additional organic compounds.

13. The process as claimed in claim 11, wherein the dehydration step is carried out by membrane separation, by distillation or by pressure swing adsorption.

14. The process as claimed in claim 1, wherein the acid/alcohol mole ratio is between 1.05 and 3.

* * * * *